United States Patent
Kim et al.

(10) Patent No.: US 10,932,732 B2
(45) Date of Patent: Mar. 2, 2021

(54) RADIATION SHIELDING DEVICE

(71) Applicant: Samsung Life Public Welfare Foundation, Seoul (KR)

(72) Inventors: Sang Hun Kim, Seoul (KR); Sung Ryong Kim, Gyeonggi-do (KR); Pyoung Jeon, Seoul (KR); Won Hong Cho, Gyeonggi-do (KR)

(73) Assignee: Samsung Life Public Welfare Foundation, Seoul (KR)

( * ) Notice: Subject to any disclaimer, the term of this patent is extended or adjusted under 35 U.S.C. 154(b) by 0 days.

(21) Appl. No.: 16/615,520

(22) PCT Filed: Oct. 12, 2017

(86) PCT No.: PCT/KR2017/011266
§ 371 (c)(1),
(2) Date: Nov. 21, 2019

(87) PCT Pub. No.: WO2018/225900
PCT Pub. Date: Dec. 13, 2018

(65) Prior Publication Data
US 2020/0178913 A1  Jun. 11, 2020

(30) Foreign Application Priority Data

Jun. 7, 2017 (KR) .................. 10-2017-0070961
Oct. 11, 2017 (KR) .................. 10-2017-0131655

(51) Int. Cl.
*A61B 6/10* (2006.01)
*G21F 1/08* (2006.01)
(Continued)

(52) U.S. Cl.
CPC .............. *A61B 6/107* (2013.01); *A61B 6/504* (2013.01); *G21F 1/085* (2013.01); *G21F 3/00* (2013.01)

(58) Field of Classification Search
CPC ......... A61B 6/107; A61B 6/504; G21F 1/085; G21F 3/00
(Continued)

(56) References Cited

U.S. PATENT DOCUMENTS 6,307,914 B1 * 10/2001 Kunieda .................. A61B 6/12
378/65
6,325,538 B1  12/2001 Heesch
(Continued)

FOREIGN PATENT DOCUMENTS

JP  2010-68990 A   4/2010
JP  2010-279622 A  12/2010
(Continued)

OTHER PUBLICATIONS

International Search Report and Written Opinion prepared by the Korean Intellectual Property Office, acting as the International Search Authority, for international application PCT/KR2017/011266 dated Mar. 7, 2018.

*Primary Examiner* — Nicole M Ippolito
(74) *Attorney, Agent, or Firm* — McCarter & English, LLP (57) ABSTRACT

Provided is a radiation shielding device according to various embodiments. The radiation shielding device includes: a body structure forming a receiving space receiving a user's body part, wherein a through passage penetrating an inside of the body structure is formed in the body structure; a shielding unit positioned to reciprocatively move along the through passage, wherein a shielding pad configured to shield the radiation is included in a portion of the shielding unit; and a driver configured to transfer a driving force to the shielding unit to cause the shielding unit to reciprocatively move.

15 Claims, 10 Drawing Sheets

(51) Int. Cl.
*G21F 3/00* (2006.01)
*A61B 6/00* (2006.01)

(58) Field of Classification Search
USPC ......... 250/505.1, 506.1, 515.1, 516.1, 517.1, 250/518.1, 519.1
See application file for complete search history.

(56) References Cited

U.S. PATENT DOCUMENTS

| | | | |
|---|---|---|---|
| 2001/0027260 A1* | 10/2001 | Uematsu | A61N 5/1048 |
| | | | 600/1 |
| 2004/0200965 A1* | 10/2004 | Umegaki | A61B 6/037 |
| | | | 250/363.1 |
| 2014/0328446 A1* | 11/2014 | Sugihara | A61B 6/032 |
| | | | 378/4 |
| 2015/0085982 A1* | 3/2015 | Willcut | G21K 1/025 |
| | | | 378/65 |
| 2019/0314643 A1* | 10/2019 | Enger | A61N 5/1007 |

FOREIGN PATENT DOCUMENTS

| | | |
|---|---|---|
| KR | 10-1358290 B1 | 2/2014 |
| KR | 10-2015-0079229 A | 7/2015 |
| KR | 10-2016-0112288 A | 9/2016 |
| KR | 10-1689473 B1 | 12/2016 |
| WO | WO 2017/083437 A1 | 5/2017 |

* cited by examiner

RADIATION SHIELDING DEVICE

CROSS-REFERENCE TO RELATED APPLICATIONS

This application is the National Stage entry under 35 U.S.C. § 371 of International Application Number PCT/KR2017/011266 filed on Oct. 12, 2017, published on Dec. 13, 2018 under publication number WO 2018/225900 A1, which claims the benefit of priority under 35 § 119 of Korean patent application number 10-2017-0070961 filed Jun. 7, 2017 and Korean patent application number 10-2017-0131655 filed Oct. 11, 2017.

TECHNICAL FIELD

The disclosure relates to a radiation shielding device, and more particularly, to a radiation shielding device used for medical purposes.

BACKGROUND ART

Generally, X-ray equipment is equipment that images the inside of a subject by detecting radiation penetrating the subject by using an X-ray detector. The X-ray equipment is used in various ways for a patient's diagnosis in a hospital, non-destructive inspection of testing materials in a laboratory, etc. However, radiation emitted from X-ray equipment used for diagnostic purposes is harmful to human bodies. When human bodies are exposed to radiation (although the radiation is a small amount), gene or cell transformation may occur, which may cause various cancers. Furthermore, genetic variation does not just affect one generation but passes down to the next generation. Therefore, it is a matter of common knowledge that human bodies should be prevented from being exposed to excessive radiation or being unnecessarily exposed to radiation.

Particularly, the thyroid located in the neck is a target organ having very high expression probability of cancer due to radiation. For proper protection against radiation, the neck needs to be shielded from radiation. However, because artifacts, particularly, metal artifacts, etc. are generated in diagnostic images acquired by radiography, there are difficulties in proper protection against radiation.

Furthermore, when X-ray equipment for emitting radiation in various directions to photograph a part of a body is used, a shielding device for protecting the thyroid against radiation needs to move according to a change of a direction in which the radiation is emitted. However, a typical shielding device has difficulties in changing its position whenever an emitting direction of radiation changes, and accordingly, it is difficult to prevent the thyroid from being exposed to radiation during serial radiography.

DESCRIPTION OF EMBODIMENTS

Technical Problem

Provided is a radiation shielding device capable of minimizing radiation exposure of a positioned body part by changing a position of a shielding pad in correspondence to a change of an emitting direction of radiation.

Solution to Problem

A radiation shielding device according to an aspect of the disclosure includes: a body structure forming a receiving space receiving the user's body part, wherein a through passage penetrating an inside of the body structure is formed in the body structure; a shielding unit positioned to reciprocatively move along the through passage, wherein a shielding pad configured to shield the radiation is included in a portion of the shielding unit; and a driver configured to transfer a driving force to the shielding unit to cause the shielding unit to reciprocatively move.

According to an example of the radiation shielding device, the shielding unit may have a plate shape, the shielding unit being longer than a length of the through passage.

According to another example of the radiation shielding device, the shielding unit may further include a plurality of transmitting pads positioned in a portion of the shielding unit and configured to transmit the radiation, and the shielding pad may be positioned between the plurality of transmitting pads According to another example of the radiation shielding device, the shielding pad may be formed with a first color, and the plurality of transmitting pads may be formed with a second color that is different from the first color.

According to another example of the radiation shielding device, the radiation shielding device may include a winding roll rotatably installed on an outer side of the body structure, connected to one end of the shielding unit, and configured to receive a driving force of the driver and wind the shielding unit.

According to another example of the radiation shielding device, a radiation shielding area in the receiving space may change when the shielding pad reciprocatively moves.

According to another example of the radiation shielding device, the body structure may include: a resting portion on which the user's body part is rested; and a first support and a second support positioned respectively at both sides of the resting portion, wherein the through passage may extend from the first support toward the second support through the resting portion.

According to another example of the radiation shielding device, the first support, the second support, and the resting portion may form a U-shaped recessed surface.

According to another example of the radiation shielding device, the shielding pad may be configured to shield at least one of radiation toward the first support, radiation toward the second support, and radiation toward the resting portion.

According to another example of the radiation shielding device, the radiation shielding device may further include at least one guide roll installed respectively on the first support and the second support, and configured to guide a movement direction of the shielding unit.

According to another example of the radiation shielding device, the body structure may further include at least one through hole configured to enable a user to check a movement of the shielding unit on the through passage from an outer surface of the body structure, wherein the at least one through hole may extend from the outer surface of the body structure to the through passage.

According to another example of the radiation shielding device, the through hole may be formed in at least one of an outer side surface of the first support, an outer side surface of the resting portion, and an outer side surface of the second support.

According to another example of the radiation shielding device, the shielding pad may include a metal including at least one of lead, carbon steel, tungsten, stainless steel and titanium.

According to another example of the radiation shielding device, the body structure may further include a detachable portion detachably coupled to the radiography device.

According to another example of the radiation shielding device, the user's body part may be a neck.

Advantageous Effects of Disclosure

The radiation shielding device according to various embodiments may change a position of the shielding pad in correspondence to a change in emitting direction of radiation, thereby minimizing radiation exposure of a body part.

Also, by accurately positioning the shielding pad through the through holes, an unintended body part may be prevented from being exposed to radiation.

Also, when neurointervention is performed, radiation exposure of the thyroid that may be subject to fatal damage by long-time radiation exposure may be allowed only when the thyroid needs to be exposed to radiation. Therefore, the fatal damage or cancer occurrence of the thyroid may be minimized.

BEST MODE

A radiation shielding device according to an aspect of the disclosure includes: a body structure forming a receiving space receiving the user's body part, wherein a through passage penetrating an inside of the body structure is formed in the body structure; a shielding unit positioned to reciprocatively move along the through passage, wherein a shielding pad configured to shield the radiation is included in a portion of the shielding unit; and a driver configured to transfer a driving force to the shielding unit to cause the shielding unit to reciprocatively move.

MODE OF DISCLOSURE

Advantages and features of the embodiments and a method of achieving the advantages and features will be apparent by referring to detailed descriptions given below in connection with the accompanying drawings. However, the embodiments of the disclosure are not limited to the following embodiments, and may be implemented in various forms. That is, it has to be understood that the present disclosure includes all modifications, equivalents, and substitutes included in the concept and technical scope of the present disclosure. The embodiments given below are provided to complete the disclosure and to allow those having ordinary skill in the art to which the disclosure pertains to more completely understand the scope of the disclosure. However, when detailed descriptions about known techniques associated with the disclosure are determined to unnecessarily obscure the gist of the disclosure, the detailed descriptions will be omitted.

The terms used in this application are merely used to describe particular embodiments, and are not intended to limit the disclosure. It will be understood that the singular forms "a," "an," and "the" include plural referents unless the context clearly dictates otherwise. It will be understood that when the terms "includes," "comprises," "including," and/or "comprising," when used in this specification, specify the presence of stated features, figures, steps, components, or combination thereof, but do not preclude the presence or addition of one or more other features, figures, steps, components, members, or combinations thereof. Although the terms "first", "second", etc. may be used herein to describe various components, these components should not be limited by these terms. These terms are only used to distinguish one component from another.

Hereinafter, the embodiments of the disclosure will be described in detail with reference to the accompanying drawings. Also, the same or corresponding components in the following description with reference to the drawings will be assigned the same reference numerals, and overlapping descriptions thereof will be omitted.

Figure 1:
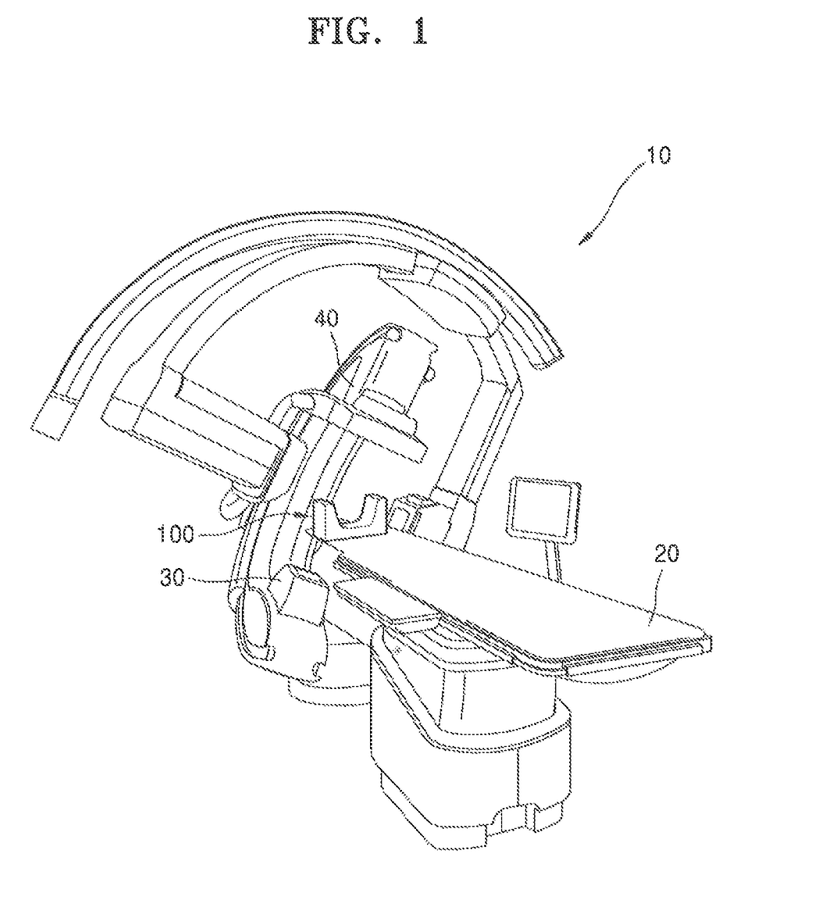
FIG. 1 schematically shows a radiography device to which a radiation shielding device is attached.

FIG. 1 schematically shows a radiography device 10 to which a radiation shielding device is attached.

Referring to FIG. 1, the radiography device 10 may include a bed 20 on which a patient (hereinafter, also referred to a user) lies, a rotating portion 40 configured to rotate in a circumferential direction of the user, and a radiating portion 30 attached to the rotating portion 40 and configured to emit radiation.

The radiography device 10 may perform radiography on a user's body part. The radiography device 10 may acquire radiography images for various directions while rotating the radiating portion 30 in the circumferential direction of the body part. For example, the radiography device 10 may emit radiation while rotating around a human's (that is, a user's) or mammal's neck and head to perform radiography on the neck and head.

The bed 20 may support the user and have a structure on which the user may lie. As shown in FIG. 1, a radiation shielding device 100 may be attached to the bed 20. Particularly, when radiography is performed on the user's neck and head, the radiation shielding device 100 may be attached to the bed 20 to receive the user's neck to protect the user's thyroid.

The radiography device 10 may emit radiation to the radiating portion 30 to photograph an inside of the user's body. The radiography device 10 may be used for angiography. The angiography is a method for showing blood vessels not shown by radiography. The angiography photographs shapes or forms of blood vessels by a contrast medium injected in the blood vessels.

More specifically, the angiography is blood vessel examination using radiation. To perform the angiography, a radiologist puts a thin conduit (having a diameter of about 2 mm) in a patient's blood vessel from outside the body and then injects a contrast medium so that the blood vessel is shown from an X-ray image. In this case, whether there is blood vessel abnormality is determined from the X-ray image to identify a disease and determine locations of lesions and the progress of disease.

The angiography may be used to select a predetermined blood vessel to perform neurointervention. In this case, various angiographies, such as 3D angio, digital subtraction angiography (DSA) road map photographing, etc., may be used.

For example, when neurointervention is performed, radiography may be performed on a neck to select a predetermined blood vessel to be treated from among blood vessels distributed in the neck, and then, to detect a blocked blood vessel, etc. from the patients head or treat the blocked blood vessel, etc., radiography may be performed on the patient's head for a long time. In this case, the radiography on the neck may be performed for a relatively short time over a total treatment time. However, because the radiography on the head being, adjacent to the neck is performed for a relatively long time, the neck's thyroid may be continuously exposed to radiation. The thyroid in the body has high expression probability of cancer when it is exposed to radiation for a long time. Accordingly, the neck's thyroid may need to be prevented from being exposed to radiation for the remaining treatment time except for when a predetermined blood vessel is selected from the neck.

Also, the above-described angiography rotates the radiating portion 30 in the circumferential direction of the head and neck to emit radiation to the head and neck so that the shapes and locations of blood vessels are determined in various directions. Accordingly, a location of a device for preventing the thyroid from being exposed to radiation may need to change in correspondence to the rotation of the radiating portion 30. According to an example, the radiation shielding device 100 according to the disclosure may rotate a shielding member for shielding radiation in a circumferential direction of a human body in correspondence to a rotation of the radiating portion 30 to minimize radiation exposure of the thyroid, which will be described in detail with reference to the drawings, below.

Figure 2:
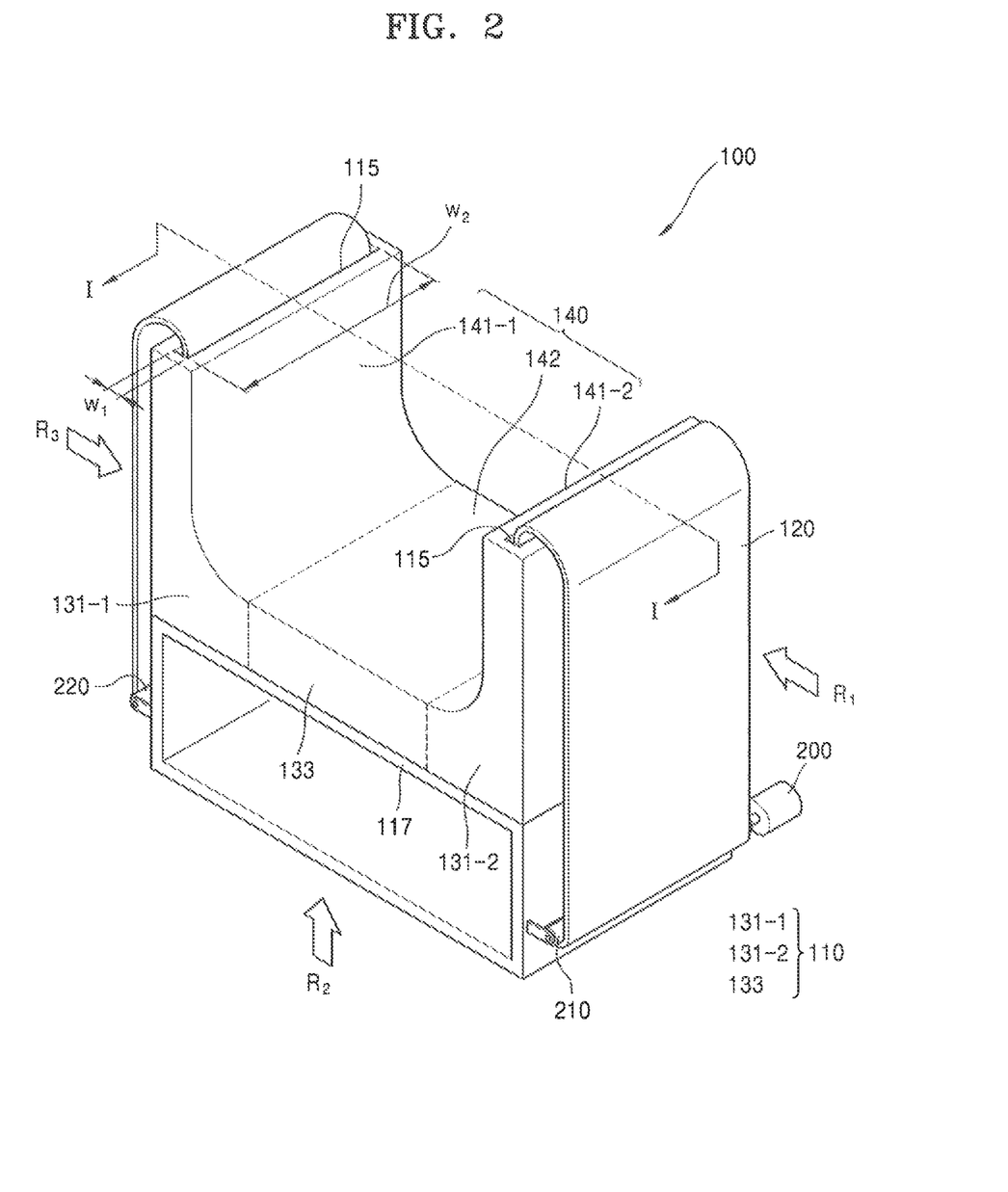
FIG. 2 is a schematic perspective view of a radiation shielding device according to an embodiment of the disclosure.

FIG. 2 is a schematic perspective view of a radiation shielding device according to an embodiment of the disclosure.

Referring to FIG. 2, the radiation shielding device 100 may include a body structure 110, a shielding unit 120, a driver 200, a first winding roll 210, a second winding roll 220, and a detachable portion 117. The body structure 110 may include a resting portion 133, a first support 131-1, and a second support 131-2.

A center portion in longitudinal direction of the body structure 110 may be recessed, and the recessed portion may form a receiving space. In the receiving space of the body structure 110, a user's body part described above with reference to FIG. 1 may be received. When the recessed portion of the body structure 110 is defined as a recessed surface 140, the recessed surface 140 may be a contact surface which the user's body part contacts. The body structure 110 may support and/or fix the user's body part received on the recessed surface 140, while surrounding the user's body part. Meanwhile, the body structure 110 may have a predetermined inclination with respect to a longitudinal direction of the recessed surface 140, and the recessed surface 140 may be formed with a shape of which thickness increases or decreases along one direction. However, the concept of the disclosure is not limited to the shape of the recessed surface 140 as long as the shape of the recessed surface 140 is selected according to a shape and characteristic of the user's body part.

For example, the body part received in the receiving space may be a user's neck, and the body structure 110 may be recessed in a U shape to correspond to the neck's shape. Meanwhile, the recessed portion of the body structure 110 may be formed in various shapes. For example, receiving spaces of various shapes, such as a V shape, a ⊏ shape, a Y shape, etc., may be formed. Hereinafter, for convenience of description, an example in which the body structure 110 is formed with a recessed side to form a U-shaped receiving space and the recessed surface 140 will be described.

The body structure 110 may include the resting portion 133, the first support 131-1 and the second support 131-2 to form the receiving space. The resting portion 133 may include a first inner surface 142 which is an inner portion of the recessed surface 140 of the body structure 110. The resting portion 133 may be in direct contact with the body part, and rest the body part on the first inner surface 142. The shielding unit 120 may be positioned in the inside of the resting portion 122, and when a shielding pad S2 (see FIG. 5) of the shielding unit 120 is positioned in the inside of the resting portion 133, the first inner surface 142 may shield radiation emitted in a second direction R2.

The first support 131-1 and the second support 131-2 may be portions of the body structure 110 positioned respectively at both sides of the resting portion 133. The first support 131-1 may include a second inner surface 141-1 which is a curved surface curved from the first inner surface 142, and the second support 131-2 may include a third inner surface 141-2 which is a curved surface curved from the first inner surface 142 and being opposite to the first inner surface 142. The second inner surface 141-1 of the first support 131-1 may contact a body part rested on the resting portion 133, and the second inner surface 141-1 of the second support 131-2 may also contact the body part rested on the resting portion 133. The first inner surface 142 to the third inner surface 141-2 may form the recessed surface 140 to surround a user's body part.

Meanwhile, when the shielding pad S2 is positioned in the inside of the first support 131-1, the second inner surface 141-1 may shield radiation emitted in a third direction R3. Likewise, when the shielding pad S2 is positioned in the inside of the second support 131-2, the third inner surface 141-2 may shield radiation emitted in a first direction R1.

An inserting opening 115 may be a hole formed at each of ends of the first support 131-1 and the second support 131-2. The inserting opening 115 may extend in a longitudinal direction of each of the ends of the first support 131-1 and the second support 131-2. The inserting opening 115 may be a hole formed in at least one shape of a rectangle, an oval, a figure with rounded edges, etc. For example, the inserting opening 115 may be a hole formed in a size and shape corresponding to a cross section of the shielding unit 120 taken along a direction that is perpendicular to a longitudinal direction L1 see FIG. 5 of the shielding unit 120 such that the shielding unit 120 is inserted in the inserting opening 115. When the cross section of the shielding unit 120 is a rectangle, the inserting opening 115 may be a rectangular hole formed in the first support 131-1 and the second support 131-2 such that the shielding unit 120 is inserted in the inserting opening 115. Meanwhile, although not shown in FIG. 2, the inserting opening 115 may be formed in a first outer side surface of the first support 131-1 being opposite to the second inner surface 141-1 and a second outer side surface of the second support 131-2 being opposite to the third inner surface 141-2. Meanwhile, the concept of the disclosure is not limited to the position of the inserting opening 115 shown in the drawings, as long as the inserting opening 115 is formed in the first support 131-1 and the second support 131-2 at locations corresponding to a height of the body part, although not shown in the drawings.

In the body structure 110, a through passage 116 (see FIG. 4) may be formed to penetrate the inside of the body structure 110 from the inserting opening 115 formed in the first support 131-1 to the inserting opening 115 formed in the second support 131-2.

Figure 5:
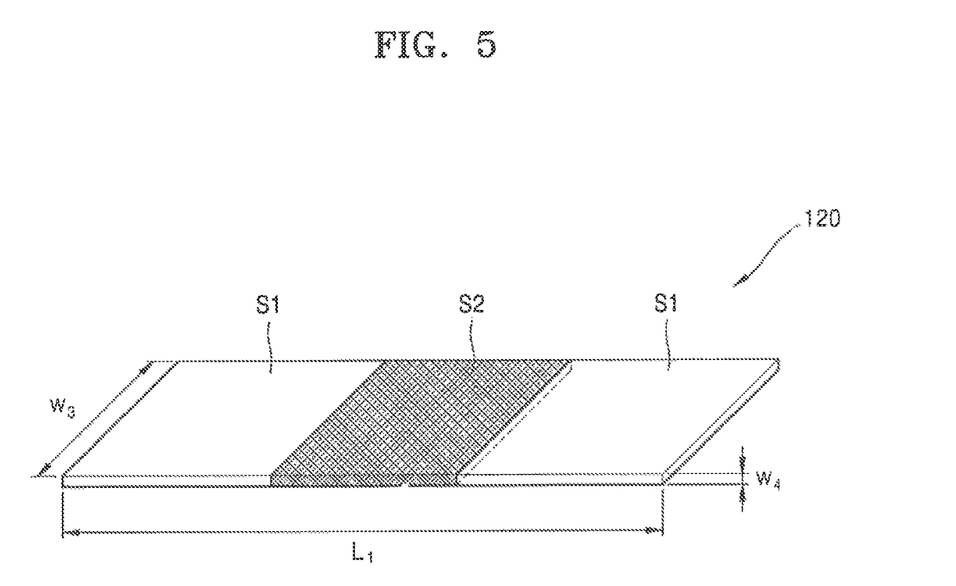
FIG. 5 is a perspective view schematically showing a shielding unit of a radiation shielding device according to an embodiment of the disclosure.

The shielding unit 120 may be in the shape of a long plate including the shielding pad S2 and a plurality of transmitting pads S1 (see FIG. 5). The shielding unit 120 may penetrate the inside of the body structure 110 via two inserting openings 115 and the through passage 116 and then surround outer side surfaces of the body structure 110. For example, the shielding unit 120 may be longer than a length of the through passage 116 so that a portion of the shielding unit 120 is positioned along the through passage 116 and the remaining portion of the shielding unit 120 is exposed to the outside of the body structure 110. That is, the shielding unit 120 may be positioned in the inside of the body structure 110 along the through passage 116, and both ends of the shielding unit 120 may be exposed to the outside of the body structure 110.

The body structure 110 may further include the detachable portion 117 that is detachable from the bed 20 shown in FIG. 1. The detachable portion 117 may be positioned on a bottom of the body structure 110, which is opposite to the recessed surface 140 of the body structure 110. The detachable portion 117 may be detachable from the bed 20 of the radiography device 10 described above with reference to FIG. 1. As shown in FIG. 2, the detachable portion 117 may include an opening hole to be coupled to the bed 20. In this case, one surface of the bed 20 may be inserted in the opening hole of the detachable portion 117 so that the body structure 110 may be fixed to the bed 20. The opening hole may have a shape corresponding to a cross section of the bed 20. For example, the opening hole of the detachable portion 117 may have a cross section of a shape corresponding to the cross section of the bed 20. When the detachable portion 117 is coupled to the bed 20, the detachable portion 117 may be coupled to the bed 20 without making any gap so that the detachable portion 117 fixes the body structure 110 to the bed 20. According to another example, the detachable portion 117 may further include a Velcro tape, a snap button, or an adhesive tape, which is capable of removably attaching the body structure 110 to the bed 20, or an elastic band which is capable of coupling the body structure 110 to the bed 20. Meanwhile, the detachable portion 117 may be integrated into the body structure 110.

The first winding roll 210 and the second winding roll 220 may be positioned respectively on both sides of the detachable portion 117 positioned on the bottom of the body structure 110, the first winding roll 210 being opposite to the second winding roll 220, so as not to interfere with radiography on the body part inserted in the body structure 110. More specifically, as shown in FIG. 2, when the first winding roll 210 is positioned on one side of the detachable portion 117, the second winding roll 220 may be positioned on the other side of the detachable portion 117, which is opposite to the one side of the detachable portion 117 on which the first winding roll 210 is positioned. In this case, radiation emitted in the first direction R1 and the third direction R3 may reach the body part without being interfered by the first winding roll 210 and the second winding roll 220.

The first winding roll 210 and the second winding roll 220, which are rollers extending in the longitudinal direction of the recessed surface 140, may be connected to both ends of the shielding unit 120 to wind or unwind the shielding unit 120. That is, the first winding roll 210 may be connected to one end of the shielding unit 120, and the second winding roll 220 may be connected to the other end of the shielding unit 120. In this case, when the first winding roll 210 and the second winding roll 220 rotate, the shielding unit 120 may move along the through passage 116.

The driver 200 may be installed in the body structure 110 to provide a driving force to the shielding unit 120 so that the shielding unit 120 reciprocatively move along the through passage 116. The driver 200 may include an electric motor or a motor which is driven by oil pressure or air pressure. However, the concept of the disclosure is not limited to the driver 200 as long as the driver 200 has a configuration capable of transmitting a driving force to the shielding unit 120 so that the shielding unit 120 reciprocatively moves along the through passage 116.

According to an embodiment, the driver 200 may rotate the first winding roll 210 and/or the second winding roll 220 respectively connected to both ends of the shielding unit 120 to transfer a driving force to the shielding unit 120, thereby causing the shielding unit 120 to reciprocatively move. The driver 200 may rotate at least one winding roll of the first winding roll 210 and the second winding roll 220 to drive the shielding unit 120. For example, the driver 200 may rotate only the first winding roll 210. In this case, the second winding roll 220 may further include an elastic member (not shown) to receive torque from its restoring force. For example, when the driver 200 rotates the first winding roll 210 to unwind one end of the shielding unit 120, the second winding roll 220 may rotate by the restoring force of the elastic member to wind the other end of the shielding unit 120. On the contrary, when the driver 200 rotates the first winding roll 210 to wind the shielding unit 120, the second winding roll 220 may rotate by the rotation of the first winding roll 210 to unwind the shielding unit 120. At this time, the elastic member included in the second winding roll 220 may accumulate a restoring force.

Meanwhile, the driver 200 may be connected directly to the shielding unit 120 to cause the shielding unit 120 to reciprocatively move. Hereinafter, for convenience of description, it is assumed that the driver 200 rotates the first winding roll 210 and the second winding roll 220. In this case, the driver 200 may rotate the first winding roll 210 and the second winding roll 220 by a rotation driving force or a linear driving force to cause the shielding unit 120 to reciprocatively move.

According to an embodiment, the radiation shielding device 100 may shield radiation emitted from the radiography device 10. The radiation shielding device 100 may transmit radiation when a body part received in the radiation shielding device 100 needs to be subject to radiography, and when the body part does not need to be subject to radiography, the radiation shielding device 100 may shield radiation. Particularly, when radiography for neurointervention is performed, the radiation shielding device 100 may cause radiation to be transmitted through a neck to select a predetermined blood vessel required for the neck, and during the subsequent treatment process, the radiation shielding device 100 may shield radiation to prevent radiation from being emitted to the neck (particularly, the thyroid). Furthermore, when a radiation irradiator of the radiography device 10 rotates in the circumferential direction of the neck and/or head, the radiation shielding device 100 may move the shielding pad S2 (see FIG. 5) for shielding radiation in correspondence to the rotation of the radiation irradiator to appropriately shield radiation to prevent the neck from being exposed to the radiation.

According to an embodiment, the radiation shielding device 100 may shield radiation at a portion of the recessed surface 140, and transmit radiation at the remaining portion. The radiation shielding device 100 may cause the shielding unit 120 positioned in the inside of the body structure 110 to reciprocatively move to change the portion of the recessed surface 140 at which radiation is shielded. For example, the radiation shielding device 100 may position the shielding pad S2 (see FIG. 5) for shielding radiation at a portion of the shielding unit 120 positioned in the inside of the body structure 110, and cause the shielding unit 120 to reciprocatively move to change a portion of the recessed surface 140 at which radiation is shielded.

Figure 3:
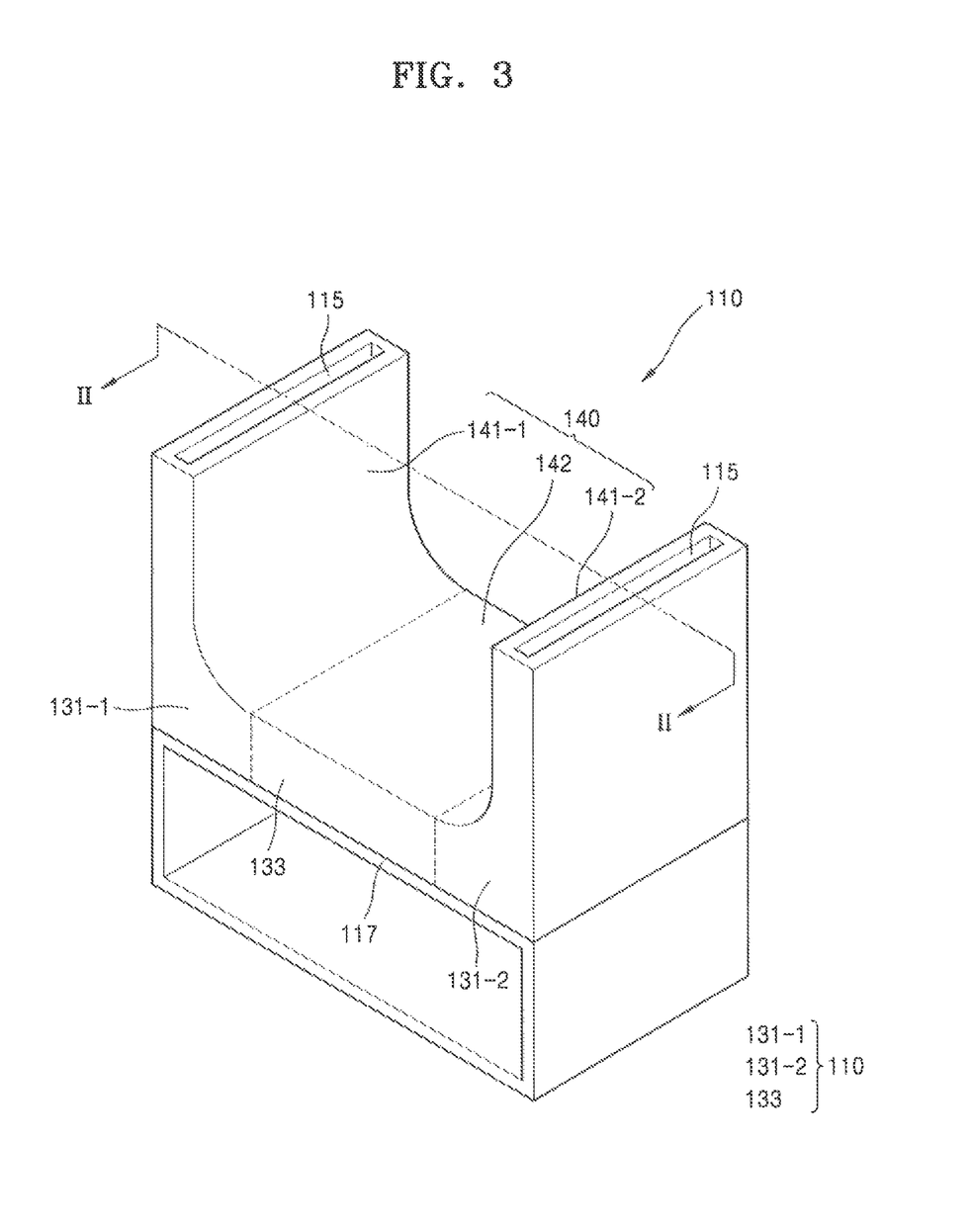
FIG. 3 is a schematic perspective view of a body structure according to an embodiment of the disclosure.
Figure 4:
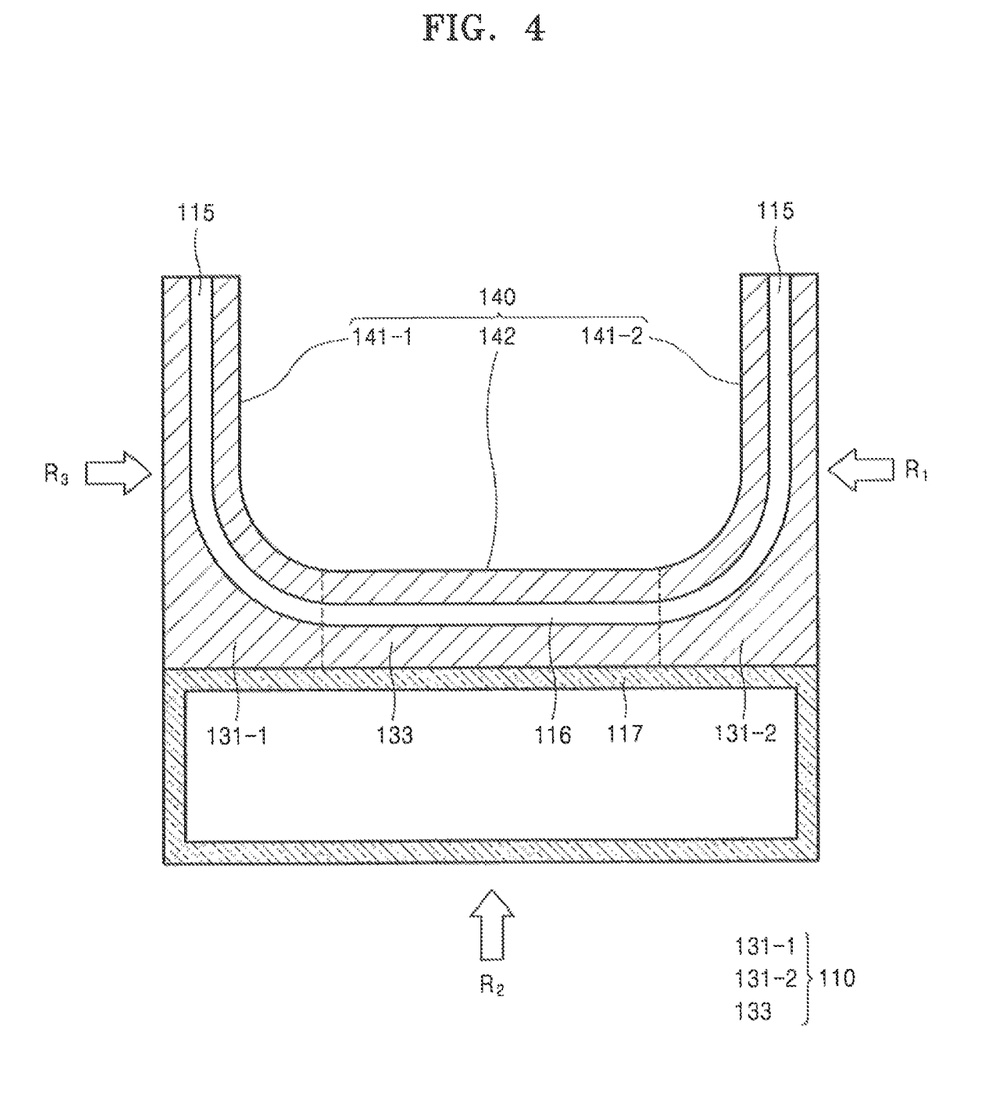
FIG. 4 is a cross-sectional view of the body structure taken along a dotted line II-II of FIG. 3.

FIG. 3 is a schematic perspective view of a body structure according to an embodiment of the disclosure, and FIG. 4 is a cross-sectional view of the body structure taken along a dotted line II-II of FIG. 3.

Referring to FIG. 3, the body structure 110 may include the resting portion 133, the first support 131-1, the second support 131-2, the inserting openings 115, and the detachable portion 117.

In the body structure 110, a receiving space may be formed in a U shape that is recessed in the longitudinal direction. A body part may be received in the receiving space. The body structure 110 may form receiving spaces of various shapes corresponding to a user's body parts.

The recessed surface 140 of the body structure 110 may be made of a cushioning material that may smoothly contact and support a user's body part received on the recessed surface 140. For example, the recessed surface 140 of the body structure 110 may be made of a cushioning and soft material, such as sponge, latex, cotton, synthetic rubber, or the like. In this case, a shape of the recessed surface 140 of the body structure 110 may change in correspondence to a shape of a user's body part.

Referring to FIG. 4, a cavity connected to the two inserting openings 115 may be formed in the body structure 110. The cavity may provide the through passage 116 along which the shielding unit 120 penetrates the body structure 110 to move. The through passage 116 may be a hole penetrating the first support 131-1, the resting portion 133, and the second support 131-2. The through passage 116 may be a passage penetrating the inside of the body structure 110 in a direction that is perpendicular to the longitudinal direction of the recessed surface 140.

The through passage 116 may have a cross section (hereinafter, referred to as a cross section of the through passage) having a shape corresponding to a shape of the inserting openings 115 and being perpendicular to a longitudinal direction of the through passage 116 so that the shielding unit 120 may reciprocatively move along the through passage 116. For example, when the shape of each inserting opening 115 is a rectangle with rounded edges, the cross section of the through passage 116 may be a rectangle with rounded edges to correspond to the shape of the inserting opening 115. Meanwhile, for example, a portion of the body structure 110 in which the through passage 116 is formed may be made of a material capable of minimizing a friction force with the shielding unit 120. For example, a surface of the portion of the body structure 110 in which the through passage 116 is formed may include a material, such as acryl, glass, etc., having a smooth surface.

According to an embodiment, the through passage 116 may form a passage of a shape corresponding to that of a cross section of the recessed surface 140 taken along a direction that is perpendicular to the longitudinal direction of the recessed surface 140. For example, when the recessed surface 140 is in a U shape, the through passage 116 may be formed as a U-shaped passage that penetrates the inside of the body structure 110.

According to an embodiment, the through passage 116 may provide a curved passage so that the shielding unit 120 may easily move in the inside of the body structure 110. For example, when the recessed surface 140 is in a ⊏ shape, the through passage 116 may provide a passage that penetrates the inside of the body structure 110 along the recessed surface 140 in such a way to be curved at bent portions of the ⊏ shape to form an overall curved passage so that the shielding unit 120 may move smoothly.

FIG. 5 is a perspective view schematically showing a shielding unit according to an embodiment of the disclosure.

Referring to FIG. 5, the shielding unit 120 may include the transmitting pads S1 for transmitting radiation and the shielding pad S2 for shielding radiation.

The shielding pad S2 may be formed with a first color, and the transmitting pads S1 may be formed with a second color that is different from the first color. The reason why the pads S1 and S2 have different colors is to enable a radiologist to easily check a movement of the shielding unit 120 on the through passage 116 through through holes 118-1, 118-2 and 118-3 of the body structure 110, which will be described later. This will be described in detail with reference to FIGS. 8 and 9, later.

The shielding unit 120 may be in the shape of a plate that reciprocatively moves along the through passage 116 of the body structure 110. A length L1 of the shielding unit 120 may be longer than a length of the through passage 116, and the shielding unit 120 may have a length enough to pass through the through passage 116 and be positioned between the first winding, roll 210 and the second winding roll 220 described above with reference to FIG. 2. Meanwhile, the shielding unit 120 may shield radiation in at least two directions of the first to third directions R1 to R3 described above with reference to FIG. 2.

The shielding unit 120 may be made of a flexible material that may be flexibly bent along the through passage 116. That is, the shielding unit 120 may move flexibly along the through passage 116 of the body structure 110, and be wound around the first winding roll 210 and the second winding roll 220 described above with reference to FIG. 4. The shielding unit 120 may be formed with a thickness $W_4$ enough to achieve a proper radiation shielding ratio of the shielding pad S2. For example, the thickness $W_4$ of the shielding unit 120 may have a value between 0.36 mm and 0.5 mm.

Both ends of the shielding unit 120 may be connected to the first winding roll 210 and the second winding roll 220, respectively. The shielding unit 120 may be wound or unwound according to a rotation of the first winding roll 210 and the second winding roll 220, and accordingly, a position of the shielding pad S2 may change in the body structure 110.

According to an embodiment, the shielding unit 120 may include the transmitting pads S1 and the shielding pad S2 arranged in the order of the transmitting pads S1, the shielding pad S2 and the transmitting pads S1 in the longitudinal direction of the shielding unit 120. In this case, the shielding pad S2 for shielding a portion of the recessed surface 140 may be appropriately positioned in the through passage 116 such that the shielding pad S1 is positioned in the inside of the body structure 110 when the shielding unit 120 passes through the through passage 116 to be positioned between the first winding roll 210 and the second winding roll 220. For example, in the shielding unit 120, the transmitting pads S1 may be formed with a length that is longer than a length between the first winding roll 210 and the inserting opening 115, from one end of the shielding unit 120, the shielding pad S2 may be formed with a length that is shorter than a length of the through passage 116, and then, the transmitting pads S1 may be formed with a length that is longer than a length between the inserting opening 115 of the second support 131-2 and the second winding roll 220.

Meanwhile, the shielding unit 120 may be long enough to position the transmitting pads S1 between the first winding roll 210 and the second winding roll 220 when the entire shielding pad S2 is wound around the first winding roll 210.

The shielding pad S2 may include a metal including at least one of lead (Pb), carbon steel, tungsten, stainless steel and titanium, a barium compound including barium sulfate (BaSO$_4$), etc. Also, an outer surface of the shielding pad S2 may be coated with a known anti-reflective coating material, for example, a resin, rubber, another non-conductive film, etc. to prevent radiation emitted from the radiation irradiator from being reflected. Meanwhile, the transmitting pads S1 may be made of a flexible and durable material that transmits radiation. Meanwhile, the shielding pad S2 may have a length enough to shield radiation in each of the first to third directions R1 to R3 or in at least two or more directions of the first to third directions R1 to R3 in the inside of the through passage 116.

Figure 6:
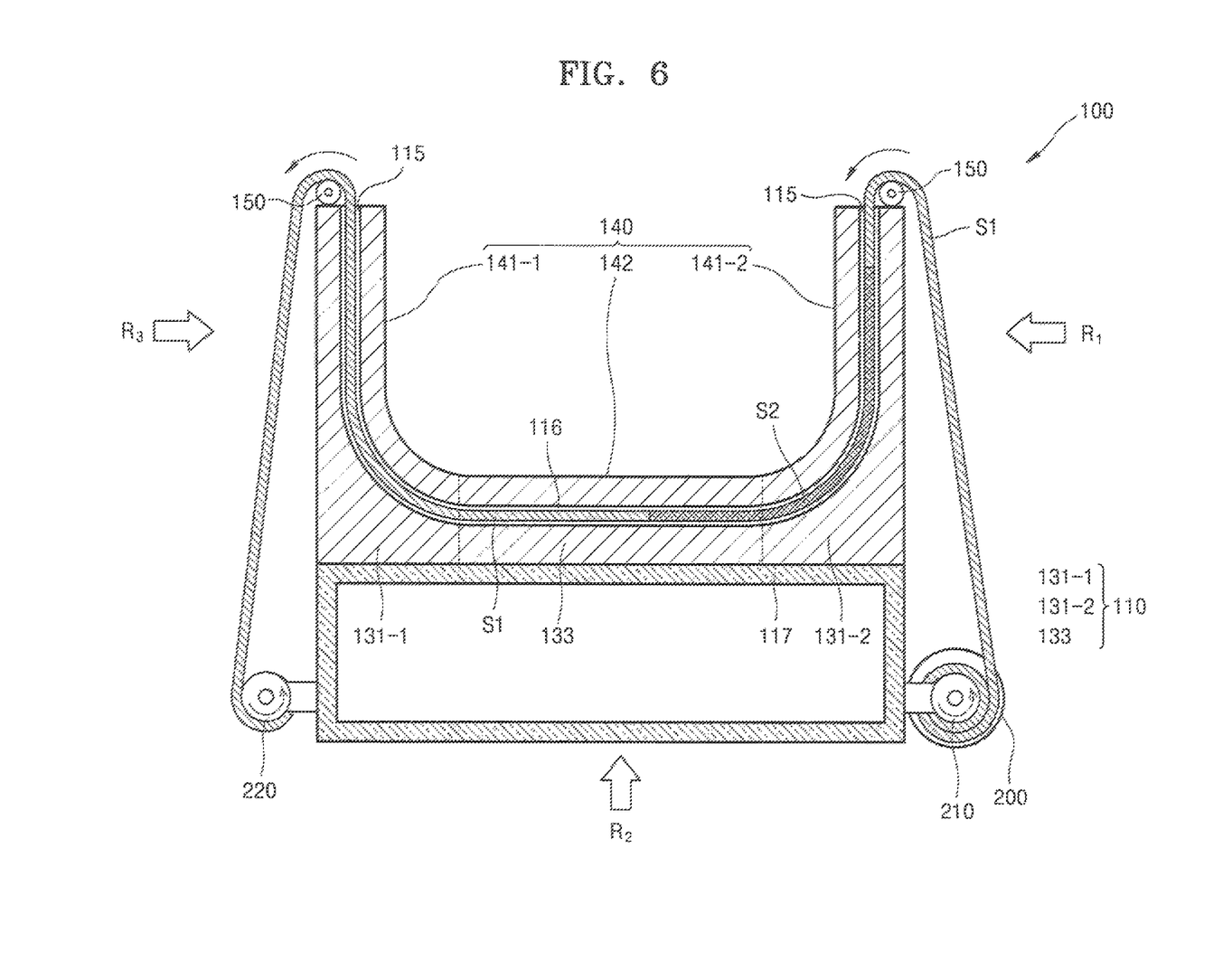
FIGS. 6 and 7 are cross-sectional views of the radiation shielding device taken along a cutting-plane line I-I of FIG. 2 for describing an operation of a shielding unit moving along a through passage.
Figure 7:
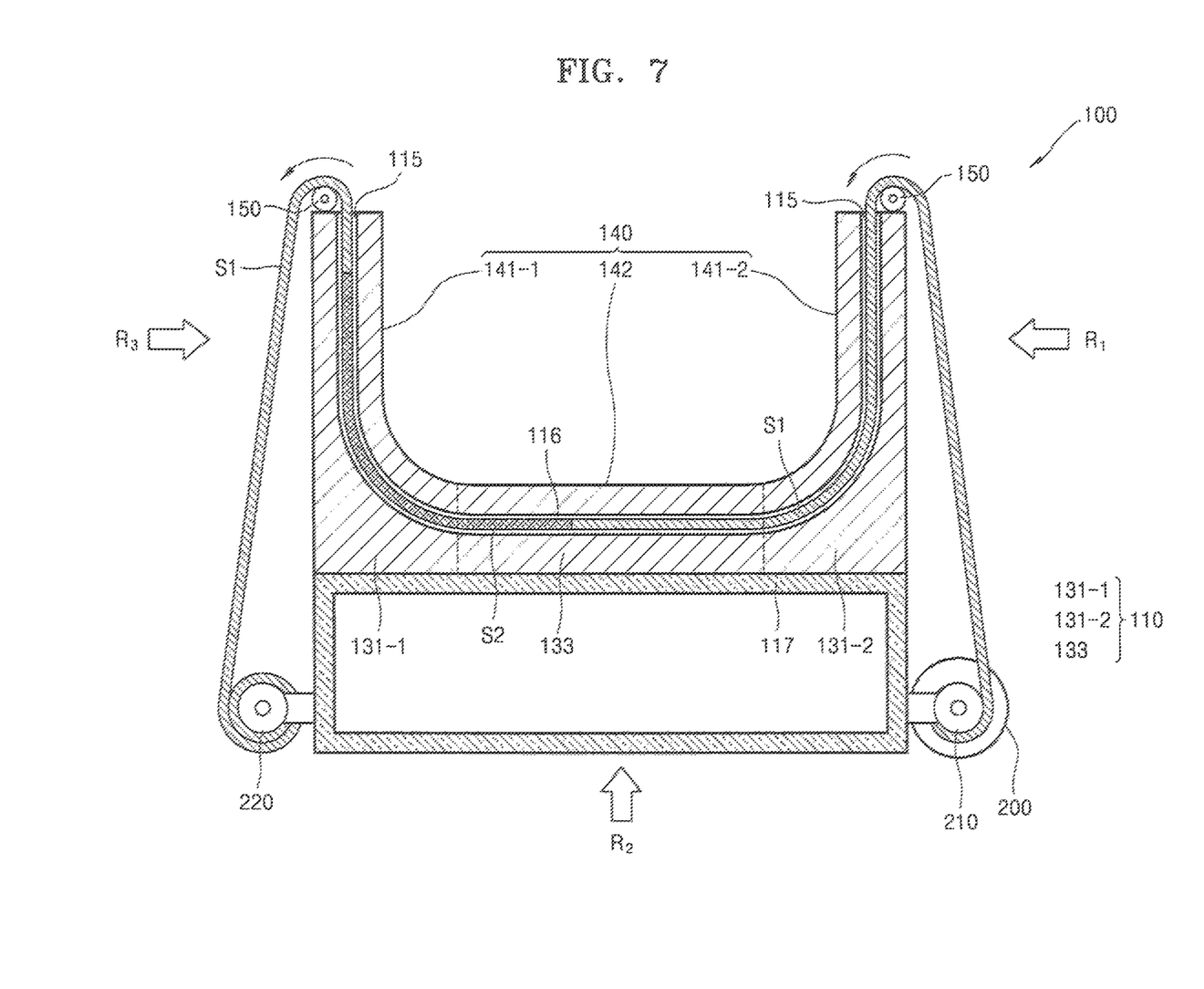

FIGS. 6 and 7 are cross-sectional views of the radiation shielding device taken along a cutting-plane line of FIG. 2 for describing an operation of a shielding unit moving along a through passage according to an embodiment of the disclosure.

Referring to FIG. 6, the shielding unit 120 may pass through the through passage 116 to extend from the first winding roll 210 to the second winding roll 220, and be wound around the first winding roll 210 and the second winding roll 220. The driver 200 may rotate the first winding roll 210 and the second winding roll 220 to cause the shielding unit 120 to reciprocatively move along the through passage 116. For example, the driver 200 may rotate the first winding roll 210 to unwind the shielding unit 120, and rotate the second winding roll 220 to wind the shielding unit 120, thereby moving the shielding unit 120 in a direction of being wound around the second winding roll 220. In this case, the shielding pad S2 may move toward the second winding roll 220. On the contrary, the driver 200 may rotate the first winding roll 210 to wind the shielding unit 120, and rotate the second winding roll 220 to unwind the first winding roll 210. In this case, the shielding pad S2 may move toward the first winding roll 210.

A guide roll 150 may be a roller that changes and guides a moving direction of the shielding unit 120 such that a portion of the shielding unit 120 escaping from the inserting opening 115 moves toward the first winding roll 210 or the second winding roll 220. The guide roll 150 may be positioned on an outer surface of the body structure 110 in contact with the shielding unit 120 such that the shielding unit 120 moves smoothly and changes its direction smoothly at an outer portion of the body structure 110 having a great curvature. For example, the guide roll 150 may be positioned around the inserting opening 115 of the first support 131-1 and around the inserting opening 115 of the second support 131-2. Also, two guide rolls 150 may be positioned respectively between a portion of the shielding unit 120 escaping from the inserting opening 115 and the first support 131-1 and between another portion of the shielding unit 120 escaping from the inserting opening 115 and the second support 131-2 to move the shielding unit 120 smoothly while minimizing friction forces with the first support 131-1 and the second support 131-2.

As shown in FIG. 6, the shielding pad S2 may be positioned in the inside of the second support 131-2 and the inside of the resting portion 133. In this case, the shielding unit 120 may shield radiation emitted in any one direction of the first direction R1 and the second direction R2. For example, the shielding unit 120 may move, by the driver 200, and the shielding pad S2 may move to the inside of the second support 131-2 and the inside of the resting portion 133 when an emitting direction of radiation emitted by the radiating portion 30 of the radiography device 10 changes from the first direction R1 to the second direction R2. That is, the radiation shielding device 100 may move the shielding unit 120 along the through passage 116 such that the shielding pad S2 of the shielding unit 120 is positioned to be opposite to an emitting direction of the radiating portion 30 of the radiography device 10.

Referring to FIG. 7, the shielding pad S2 of the shielding unit 120 may move toward the second winding roll 220 by the driver 200 to be positioned in the insides of the resting portion 133 and the first support 131-1. In this case, unlike FIG. 6, the shielding unit 120 may shield radiation emitted in any one direction between the second direction R2 and the third direction R3. That is, the shielding unit 120 shown in FIG. 7 may be at a position moved toward the second winding roll 220 along the through passage 116 from the position of the shielding unit 120 shown in FIG. 6.

According to an embodiment, the radiation shielding device 100 may drive the driver 200 to move the shielding unit 120 in correspondence to a change in emitting direction of radiation, thereby changing a position of the shielding pad S2. The radiation shielding device 100 may move the shielding pad S2 to the inside of the body structure 110 to be opposite to an emitting direction of radiation, thereby preventing a body part received on the recessed surface 140 from being exposed to radiation. For example, when the shielding pad S2 is positioned in the inside of the first support 131-1 and an emitting direction of radiation changes from the third direction R3 to the second direction R2, the radiation shielding device 100 may operate the driver 200 correspondingly such that the first winding roll 210 winds the shielding unit 120 and the second winding roll 220 unwinds the shielding unit 120, thereby positioning the shielding pad S2 of the shielding unit 120 in the insides of the first support 131-1 and the resting portion 133. Likewise, when the shielding pad S2 is positioned in the inside of the second support 131-2 and an emitting direction of radiation changes from the first direction R1 to the second direction R2, the radiation shielding device 100 may operate the driver 200 such that the first winding roll 210 unwinds the shielding unit 120 and the second winding roll 220 winds the shielding unit 120, thereby moving the shielding unit 120 along the through passage 116 to position the shielding pad S2 of the shielding unit 120 to the inside of the resting portion 133 from the inside of the second support 131-2.

According to an embodiment, when radiography is performed on a body part received on the recessed surface 140, the radiation shielding device 100 may cause the shielding pad S2 to reciprocatively move to transmit radiation. For example, when radiation is emitted in the first direction R1, the radiation shielding device 100 may move the shielding unit 120 so that the shielding pad S2 is positioned in the inside of the resting portion 133. According to another example, the radiation shielding device 100 may operate the driver 200 to move the shielding unit 120 such that the entire shielding pad S2 is wound around at least one of the first winding roll 210 and the second winding roll 220.

Thereafter, when radiography performed on the body part is completed, the radiation shielding device 100 may position the shielding pad S2 to be opposite to an emitting direction of radiation, as described above, to prevent the body part received on the recessed surface 140 from being exposed to radiation.

As such, the radiation shielding device 100 may transmit radiation to a body part received on the recessed surface 140 or shield radiation for the body part, as necessary. Furthermore, when radiation does not need to be emitted on a body part received on the recessed surface 140, the radiation shielding device 100 may operate the driver 200 to rotate the first winding roll 210 and the second winding roll 220 to cause the shielding unit 120 to reciprocatively move such that the shielding pad S2 is positioned in the inside of the body structure 110 to be opposite to an emitting direction of radiation.

In this regard, when an emitting direction of radiation changes, the radiation shielding device 100 may change a position of the shielding pad S2 correspondingly, thereby minimizing radiation exposure of a body part. Particularly, when neurointervention is performed, radiation exposure of the thyroid that may be subject to fatal damage by long-time radiation exposure may be allowed only when the thyroid needs to be exposed to radiation. Therefore, the fatal damage or cancer occurrence of the thyroid may be minimized.

Figure 8:
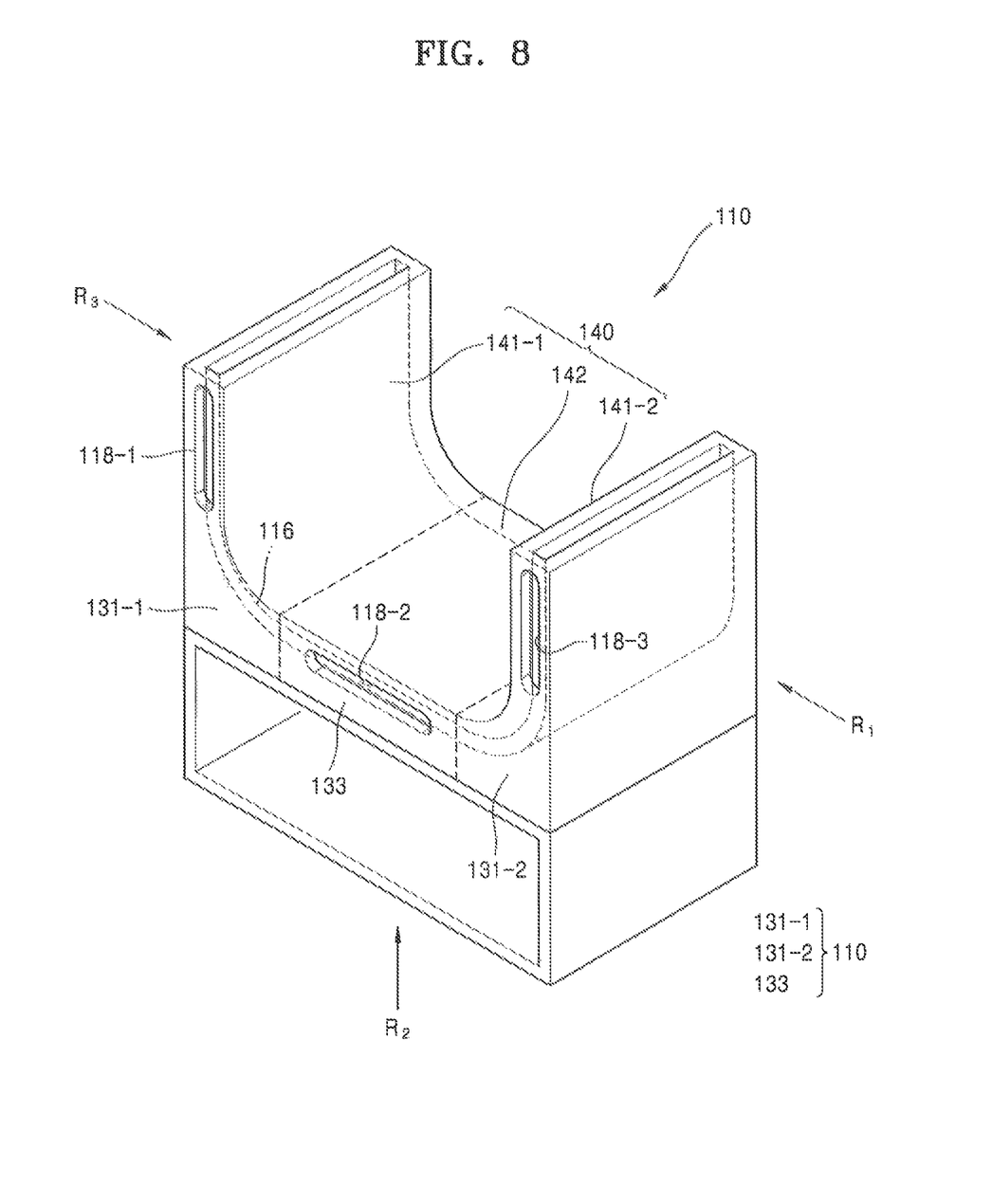
FIG. 8 is a perspective view schematically showing a through hole according to an embodiment of the disclosure.

FIG. 8 is a perspective view schematically showing a through hole according to an embodiment of the disclosure.

Referring to FIG. 8, the body structure 110 may include a first through hole 118-1, a second through hole 118-2 and a third through hole 118-3. At this time, the first to third through holes 118-1, 118-2 and 118-3 may extend from the outer surface of the body structure 110 to the through passage 116.

The first through hole 118-1 may enable a radiologist to check whether the shielding pad S2 is properly positioned in the inside of the first support 131-1 to shield radiation transmitted in the third direction R3. Similarly, the second through hole 118-2 may enable a radiologist to check whether the shielding pad S2 is properly positioned in the inside of the resting portion 133 to shield radiation transmitted in the second direction R2. Also, the third through hole 118-3 may enable a radiologist to check whether the shielding pad 32 is properly positioned in the inside of the second support 131-2 to shield radiation transmitted in the first direction R1.

However, the above-described locations and shapes of the first to third through holes 118-1, 118-2 and 118-2 may be exemplary, and the concept of the disclosure is not limited to the locations and shapes of the first to third through holes 118-1, 118-2 and 118-2. Accordingly, the first to third through holes 118-1, 118-2 and 118-2 may be formed as a single through hole, or more through holes may be formed. Also, a through hole may be formed in the recessed surface 140 of the body structure 110.

Figure 9:
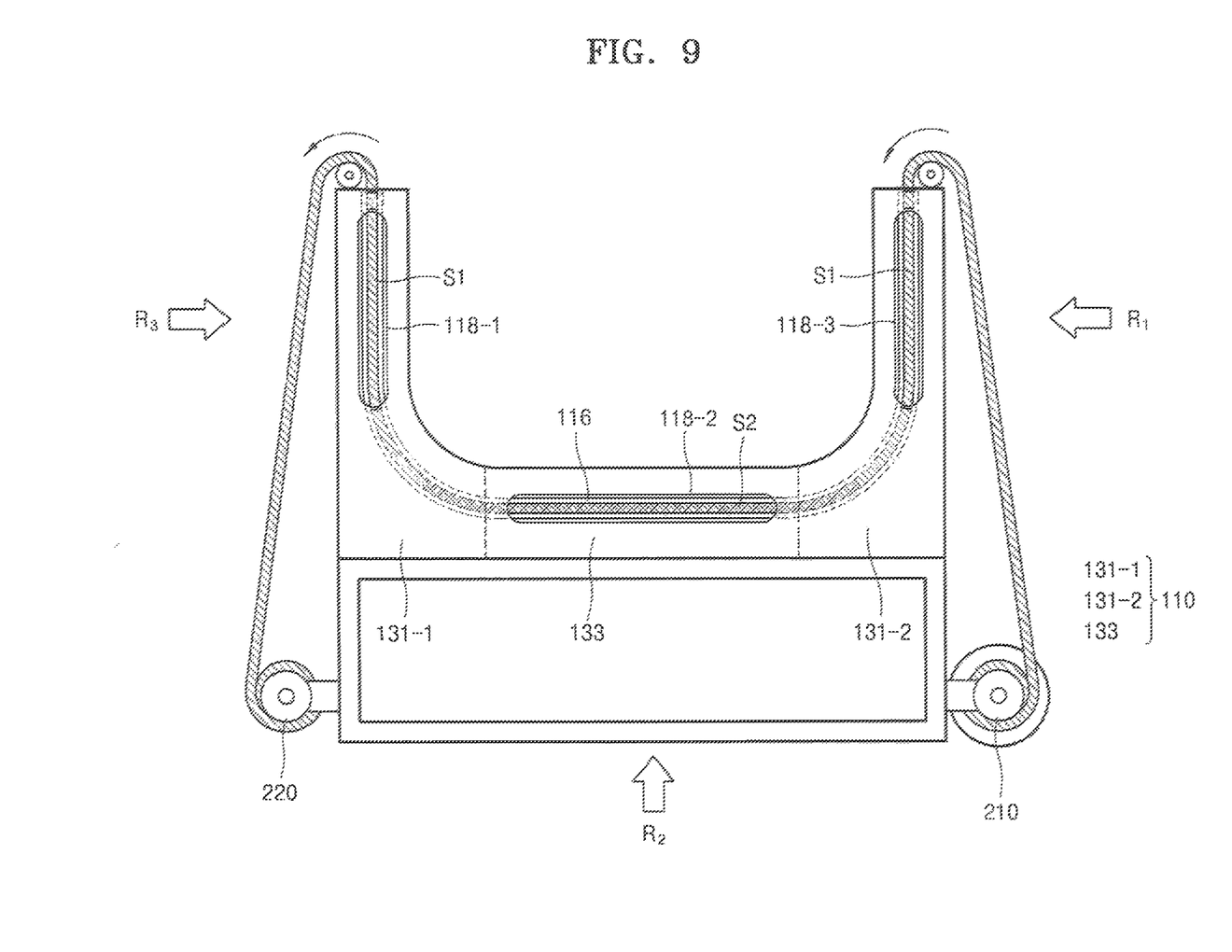
FIG. 9 is a side view for describing a method of checking a position of a shielding pad through a through hole according to an embodiment of the disclosure.

FIG. 9 is a side view for describing a method of checking a position of the shielding pad S2 through the first to third through holes 118-1, 118-2 and 118-3 according to an embodiment of the disclosure.

As described above with reference to FIG. 5, the shielding pad S2 may be formed with the first color, and the transmitting pads S1 may be formed with the second color that is different from the first color. Accordingly, a user may position the shielding pad S2 properly based on the colors of the pads S1 and S2 observed through the first to third through holes 118-1, 118-2 and 118-3.

As shown in the drawings, to shield radiation emitted in the second direction R2, a user may rotate the first winding roll 210 and the second winding roll 220 to position the shielding pad S2 in the inside of the resting portion 133. At this time, the user may appropriately rotate the first winding roll 210 and the second winding roll 220 to observe the first color of the shielding pad S2 through the second through hole 118-2.

In this way, the disclosure may accurately change a position of the shielding pad S2 when an emitting direction of radiation changes, thereby minimizing radiation exposure of a body part. Particularly, by accurately determining the position of the shielding pad S2, radiation exposure of an unintended body part may be prevented.

Figure 10:
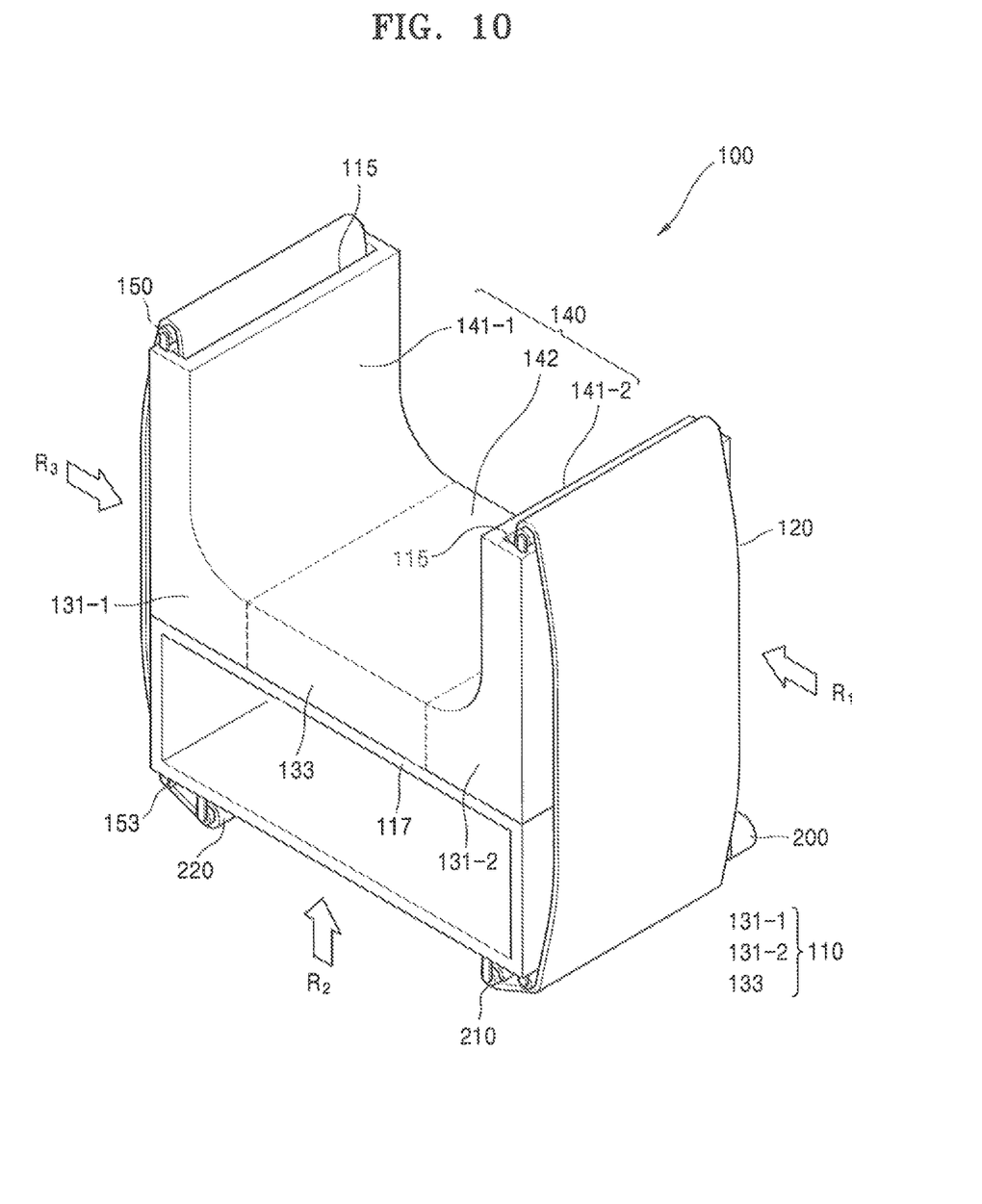
FIG. 10 is a schematic perspective view of a radiation shielding device according to an embodiment of the disclosure.

FIG. 10 is a schematic perspective view of a radiation shielding device according to an embodiment of the disclosure.

Referring to FIG. 10, the radiation shielding device 100 may include the body structure 110, the shielding unit 120, the driver 200, the guide roll 150, an auxiliary guide roll 153, the first winding roll 210, the second winding roll 220, and the detachable portion 117.

The first winding roll 210 and the second winding roll 220 may be positioned on the bottom of the detachable portion 117 that is opposite to the second direction R2 described above with reference to FIG. 2. In this case, the first winding roll 210 and the second winding roll 220 may be prevented from interfering with a rotation of the rotating portion 40 described above with reference to FIG. 1.

The auxiliary guide roll 153 may be installed on the bottom of the detachable portion 117 to guide a driving direction of the shielding unit 120 toward the first winding roll 210 and the second winding roll 220. For example, the auxiliary guide roll 153 may cause the shielding unit 120 moving in an opposite direction of the second direction R2 to change its direction to the third direction R3 or the first direction R1 to be smoothly wound around the first winding roll 210 and the second winding roll 220.

Thus, the concept of the present disclosure is not limited to the above-described embodiments, and it is intended that the disclosure covers the modifications and variations of this disclosure provided they come within the scope of the appended claims and their equivalents.

The invention claimed is:

1. A radiation shielding device for protecting a user's body part against radiation emitted from a radiography device, the radiation shielding device comprising:
    a body structure forming a receiving space receiving the user's body part, wherein a through passage penetrating an inside of the body structure is formed in the body structure;
    a shielding unit positioned to reciprocatively move along the through passage, wherein a shielding pad configured to shield the radiation is included in a portion of the shielding unit; and
    a driver configured to transfer a driving force to the shielding unit to cause the shielding unit to reciprocatively move.

2. The radiation shielding device of claim 1, wherein the shielding unit has a plate shape, the shielding unit being longer than a length of the through passage.

3. The radiation shielding device of claim 2, wherein
the shielding unit further comprises a plurality of transmitting pads positioned in a portion of the shielding unit and configured to transmit the radiation, and
the shielding pad is positioned between the plurality of transmitting pads.

4. The radiation shielding device of claim 3, wherein the shielding pad is formed with a first color, and the plurality of transmitting pads are formed with a second color that is different from the first color.

5. The radiation shielding device of claim 1, further comprising a winding roll rotatably installed on an outer side, of the body structure, connected to one end of the shielding unit, and configured to receive a driving force of the driver and wind the shielding unit.

6. The radiation shielding device of claim 1, wherein a radiation shielding area in the receiving space changes when the shielding pad reciprocatively moves.

7. The radiation shielding device of claim 1, wherein the body structure comprises:
a resting portion on which the user's body part is rested; and
a first support and a second support positioned respectively at both sides of the resting portion,
wherein the through passage extends from the first support toward the second support through the resting portion.

8. The radiation shielding device of claim 7, wherein the first support, the second support, and the resting portion form a U shaped recessed surface.

9. The radiation shielding device of claim 7, wherein the shielding pad is configured to shield at least one of radiation toward the first support, radiation toward the second support, and radiation toward the resting portion.

10. The radiation shielding device of claim 7, further comprising at least one guide roll installed respectively on the first support and the second support, and configured to guide a movement direction of the shielding unit.

11. The radiation shielding device of claim 7, wherein the body structure further comprises
at least one through hole configured to enable a user to check a movement of the shielding unit on the through passage from an outer surface of the body structure,
wherein the at least one through hole extends from the outer surface of the body structure to the through passage.

12. The radiation shielding device of claim 11, wherein the through hole is formed in at least one of an outer side surface of the first support, an outer side surface of the resting portion, and an outer side surface of the second support.

13. The radiation shielding device of claim 1, wherein the shielding pad comprises a metal including at least one of lead, carbon steel, tungsten, stainless steel and titanium.

14. The radiation shielding device of claim 1, wherein the body structure further comprises a detachable portion detachably coupled to the radiography device.

15. The radiation shielding device of claim 1, wherein the user's body part is a neck.

* * * * *